United States Patent
Danielmeier et al.

(10) Patent No.: US 6,222,066 B1
(45) Date of Patent: Apr. 24, 2001

(54) PROCESS FOR DECREASING THE CHLORINE CONTENT OF ORGANIC ISOCYANATES

(75) Inventors: Karsten Danielmeier, Bethel Park, PA (US); Harald Leps; Dieter Mager, both of Leverkusen (DE); Reinhard Halpaap; Martin Brahm, both of Odenthal (DE); Reinhold Klipper, Köln (DE); Andreas Hauner, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/532,259

(22) Filed: Mar. 22, 2000

(30) Foreign Application Priority Data

Mar. 30, 1999 (DE) ............................. 199 14 292

(51) Int. Cl.$^7$ ................................. C07C 249/00
(52) U.S. Cl. .................................... 560/352
(58) Field of Search ............................ 560/352

(56) References Cited

U.S. PATENT DOCUMENTS

| | | | |
|---|---|---|---|
| 3,219,678 | 11/1965 | Kober et al. | 260/453 |
| 3,264,336 | 8/1966 | Powers | 260/453 |
| 3,373,182 | 3/1968 | Powers | 260/453 |
| 3,458,558 | 7/1969 | Cheng | 260/453 |
| 3,549,504 | 12/1970 | Adica et al. | 203/49 |
| 3,759,971 | 9/1973 | Cuscurida et al. | 260/453 SP |
| 3,793,362 | 2/1974 | Kolakowski et al. | 260/453 SP |
| 3,799,963 | 3/1974 | Adams | 260/453 SP |
| 3,840,578 | 10/1974 | Hennig | 260/453 SP |
| 3,853,936 | 12/1974 | Van Winkle | 260/453 SP |
| 3,857,871 | 12/1974 | Hatfield, Jr. et al. | 260/453 SP |
| 3,989,650 | 11/1976 | Lange et al. | 260/2.1 E |
| 4,094,894 | 6/1978 | Blackwell | 260/453 SP |
| 4,160,080 | 7/1979 | Köenig et al. | 528/39 |
| 4,294,666 | 10/1981 | Astheimer et al. | 203/72 |
| 4,996,351 | 2/1991 | Nafziger | 560/352 |
| 5,362,399 | * 11/1994 | Schwarz et al. | |
| 5,386,054 | 1/1995 | Scholl et al. | 560/352 |
| 5,756,063 | * 5/1998 | Nuernberg et al. | |

FOREIGN PATENT DOCUMENTS

| | | |
|---|---|---|
| 1138040 | 10/1962 | (DE) . |
| 1270036 | 6/1968 | (DE) . |
| 1950101 | 4/1971 | (DE) . |
| 285593 | 12/1990 | (DE) . |
| 288594 | 4/1991 | (DE) . |
| 288595 | 4/1991 | (DE) . |
| 288596 | 4/1991 | (DE) . |
| 288597 | 4/1991 | (DE) . |
| 288598 | 4/1991 | (DE) . |
| 288599 | 4/1991 | (DE) . |
| 1034357 | 6/1966 | (GB) . |
| 1080717 | 8/1967 | (GB) . |
| 1186896 | 4/1970 | (GB) . |
| 1229181 | 4/1971 | (GB) . |
| 1347647 | 2/1974 | (GB) . |
| 1362708 | 8/1974 | (GB) . |
| 1384065 | 2/1975 | (GB) . |
| 1458747 | 12/1976 | (GB) . |
| 1459691 | 12/1976 | (GB) . |
| 1570741 | 7/1977 | (GB) . |
| 1517162 | 7/1978 | (GB) . |
| 67004137 | 2/1967 | (JP) . |
| 70010329 | 12/1970 | (JP) . |
| 59-088452 | 5/1984 | (JP) . |
| 59-172450 | 9/1984 | (JP) . |
| 61161250 | 7/1986 | (JP) . |
| 1052747 | 2/1989 | (JP) . |
| 5058982 | 3/1993 | (JP) . |
| 5163231 | 6/1993 | (JP) . |
| 6345707 | 12/1994 | (JP) . |
| 7278088 | 10/1995 | (JP) . |
| 9323968 | 12/1997 | (JP) . |
| 806677 | 5/1982 | (SU) . |
| 8100606 | 7/1982 | (ZA) . |

* cited by examiner

Primary Examiner—Gary Geist
Assistant Examiner—John N. Calve
(74) Attorney, Agent, or Firm—Joseph C. Gil; Lyndanne M. Whalen

(57) ABSTRACT

A process for the purification of organic isocyanates or isocyanate mixtures in which the amount of chlorine compound(s) present is reduced by mixing the isocyanate(s) or isocyanate mixtures with a gel-type or macroporous, anion-exchanging organic material having tertiary and/or quaternary amino groups. The process renders possible a purification of the isocyanates from chlorine-containing compounds which is milder than in conventional processes and is therefore particularly suitable for temperature-sensitive isocyanates.

10 Claims, No Drawings

PROCESS FOR DECREASING THE CHLORINE CONTENT OF ORGANIC ISOCYANATES

BACKGROUND OF THE INVENTION

This invention relates to a new process for the purification of organic isocyanates or isocyanate mixtures by removing chlorine compounds. In this process, the isocyanate or isocyanate mixture is mixed with a gel-type or macroporous, anion-exchanging organic material having tertiary and/or quaternary amino groups. The process renders possible a purification of the isocyanates from chlorine-containing compounds under milder conditions than those used in conventional purification processes and is therefore particularly suitable for treating temperature-sensitive isocyanates.

Impurities of varying type and quantity which arise during production of isocyanates are a cause of fluctuation in activity of the isocyanate. Such fluctuations in activity are a disadvantage because reproducible results can not be obtained. Both aromatic isocyanates (for example, the well-known phosgenation products of aniline-formaldehyde condensates and 2,4-and 2,6-toluenediisocyanate) and aliphatic isocyanates (such as isophorone diisocyanate) contain an abundance of such impurities. These impurities include chlorine-containing compounds which invariably cause fluctuations in activity when "freely mobile" (so-called "hydrolyzable") chlorine is involved. A proportion of these chlorine-containing compounds proves to be relatively stable and remains in the isocyanate(s) even after distillation. This proportion adversely affects the stability of the isocyanates, as well as their activity. A uniform, low proportion of these impurities with a resulting standardization of the activity and easier processing of the isocyanates is therefore important both technically and economically.

There have accordingly been many attempts to find possible ways to remove the chlorine-containing compounds. Thermal processes are described in a multitude of published patent applications. It is known, for example, that heating of isocyanates, in particular with simultaneous stripping with inert gas, or heating in inert solvents under pressure with simultaneous removal of the volatile compounds by filtration under suction, decreases the content of readily decomposable chlorine compounds. (See, for example, DE-A 1,270,036; DD 271,820; U.S. Pat. No. 3,219,678; GB-A 1,080,717; DE-A 2,237,552; U.S. Pat. No. 3,857,871; U.S. Pat. No. 1,458,223; JP 0 727 808 8 A2; JP 0 634 570 7 A2; and GB-A 1,384,065.)

JP 6 116 125 A; JP 0 516 323 1 A; DE-A 1,950,101; DE-A 1,938,384; DE-A 2,532,722; DE-A 2,631,168; U.S. Pat. No. 3,853,936; FR-A 1,555,517; DE-A 2,933,601; and U.S. Pat No. 3,549,504 each disclose that isocyanates can be purified by specific distillation and crystallization techniques. However, efficient separation of the interfering chlorine compounds is not achieved by any of these processes which are based on a purely physical treatment. Only readily decomposable chlorine compounds can be separated by these treatments. The usefulness of processes of this type is therefore limited to specific, generally thermostable, isocyanate compounds that can be used even with limited lowering of the chlorine content.

In addition to purely thermal treatments of isocyanate compounds, treatments with additives which allow an improved separation of interfering chlorine compounds are also described in the prior art. JP 4 501 032 9 B; JP4 2,004,137 B; JP59,088,452A; JP5,910,875 3A;JP 59,172, 450A; U.S. Pat. No. 3,373,182; GB-A 1,111,581; U.S. Pat. No. 3,759,971; U.S. Pat. No. 4,094,894; ZA-A 8,100,606; DE-A 1,138,040; DE-A 1,286025; U.S. Pat. No. 3,458,558; U.S. Pat. No. 3,264,336; JP 01,052,747 A2; SU 806,677; and DE-A 2,210,607 disclose processes using additives based on metals or on alkali metals, for example, metal oxides, metal cyanamides, metal hydrides, metal fatty acid esters in the presence of sterically hindered phenols, metal naphthenates, metal silicates, alkali metal carbonates, organometallic compounds or (alkali) metal-containing synthetic zeolites. But in some cases these additives cannot be satisfactorily separated from the purified isocyanate and lead to unwanted metal/metal ion contamination of the corresponding isocyanate products. In addition, almost all metals and metal complexes give rise to an increased formation of secondary products (formation of trimers, carbodiimides, dimers).

Similar limitations are found with the use of additives such as the imidazole described in GB-A 1,347,647 and JP 0 505 898 2 A; the sulfonic acids and their esters described in GB-A 1,458,747; the diethyl sulfate described in GB-A 1,459,691 and the sulfuric acid also described in GB-A 1,459,691; as well as with the use of other additives such as, for example, epoxy compounds (DE-A 2,249,375; JP 0 932 396 8 A2), tetra-substituted ureas (DD 288 598), formic acid or acetic acid or their derivatives (U.S. Pat. No. 3,799,963) or the compounds containing trimethylsilyl groups described in EP-A 524 507. The described use of dissolved acids and bases, especially in the purification of reactive isocyanate compounds, leads to unwanted secondary reactions such as trimerization, dimer formation or carbodiimide formation.

Several compounds having at least one Zerewitinoff-active NH group, such as ureas (DD 285 594), biurets (DD 288 597), caprolactam (DD 285 593), epoxides in the presence of amines (JP 0 932 396 8 A2), as well as ammonium salts (DD 288 594), carbodiimides (DD 288 599), alkyl phosphates (DD 288 596), tertiary alcohols and tertiary alkyl carbamates (DD 288 595) are recommended in prior art for the purification of isocyanates. Here, too, there is the disadvantage of incomplete separation of the additives and limited use of the additive-containing isocyanates and/or distillation residues. In particular, the presence of additives may sometimes cause a significant decrease in the NCO value and an increase in viscosity, which can be attributed, for example, to the formation of biurets when tertiary alcohols are used. Increased viscosity due to formation of unwanted by-product formation also occurs when water is used to purify isocyanates (DE-A 1,240,849). U.S. Pat. No. 4,996,351 describes the use of polymeric, strongly acidic material, having $pK_a$ values of $\leq 2$ to lower the quantity of hydrolyzable chlorine. In the patent examples, the polymeric, strongly acidic material is added to the boiling isocyanate to effectively lower the content of hydrolyzable chlorine. Inorganic acids and strongly acidic organic compounds are described as effective catalysts for allophanate formation (for example, U.S. Pat. No. 4,160,080). However, such acidic compounds greatly promote corrosion and are not therefore very suitable for decreasing the hydrolyzable chlorine content of organic isocyanates.

Patent DD 288 593 describes the use of salts of primary and secondary amines as additives for lowering the content of hydrolyzable chlorine. At temperatures of at least 200° C. and with the simultaneous addition of inert gases, these salts allow an effective lowering of the content of hydrolyzable chlorine. In the examples, temperatures of 225° C. are said to be necessary for an effective lowering of hydrolyzable chlorine. These high temperatures limit the application of the process to a few relatively thermostable isocyanates.

According to generally accepted doctrine, isocyanate compounds, in particular temperature-sensitive low-molecular isocyanates, are not stable at such high temperatures and decompose to form unwanted by-products such as carbodiimides and isocyanurates. This can lead to an uncontrolled formation of process heat, which renders management of the reaction far more difficult. Furthermore, use of inert gas which DD 288 593 teaches to be necessary inevitably leads to a highly contaminated flow of waste gas that is potentially harmful to the environment and a safety hazard. Finally, it is difficult to separate the described salts of primary and secondary amines from purified low-molecular isocyanates by means of distillation, extraction or other known techniques because, as described in DD 288 593, the unwanted reaction of amine salt with the isocyanate(s) to be purified leads to high losses in yield and formation of secondary products.

SUMMARY OF THE INVENTION

It is an object of the present invention to provide a universally applicable process for the purification of organic low-molecular weight isocyanates which does not have the shortcomings discussed and renders possible an efficient separation of the isocyanate from the reagents used in order to lower the content of hydrolyzable chlorine.

It is another object of the present invention to provide a process for significantly reducing the hydrolyzable chlorine content of temperature sensitive low molecular weight isocyanates which does not cause formation of unwanted by-products.

These and other objects which will be apparent to those skilled in the art are accomplished by adding a suitable quantity of a gel-type or macroporous, anion-exchanging organic material having tertiary and/or quaternary amino groups, which is described in more detail below, to the organic isocyanate(s) or isocyanate mixtures to be treated and heating the mixture for a definite period, optionally under increased or reduced pressure.

Surprisingly, the process of the present invention permits effective separation of interfering chlorine compounds (lowering of the content of hydrolyzable chlorine) at temperatures far below 200° C. without the need to use inert gas, without use of acid conditions and without the formation of significant quantities of secondary products.

DETAILED DESCRIPTION OF THE INVENTION

That use of gel-type or macroporous, anion-exchanging organic materials having tertiary and/or quaternary amino groups effectively lowered the quantity of hydrolyzable chlorine was surprising because low-molecular weight tertiary and quaternary amines and amine salts are known to be trimerization catalysts and would therefore be expected to have a tendency to form secondary products.

The present invention provides a process for the purification of low-molecular weight isocyanates from chlorine compounds. In this process, at least 0.1 wt. % (based on isocyanate) of a gel-type or macroporous anion exchanging organic material containing tertiary and/or quaternary amino groups, which is substantially free from metal ions, water and solvents or admixtures thereof which react with isocyanates, is added to the low-molecular isocyanate(s) or isocyanate mixture, and heated at a temperature of <200° C. for at least 10 minutes. Subsequently, the isocyanate or isocyanate mixture may be freed from the gel-type or macroporous, anion-exchanging organic material having tertiary and/or quaternary amino groups and from reaction products which may have formed by filtration, distillation, extraction, any other separation techniques known in the art and combinations thereof.

Starting materials for the process of the present invention may be any low-molecular weight isocyanate. As used herein, the term "isocyanate" includes a single low molecular weight isocyanate, more than one low molecular weight isocyanate, and any mixtures of low-molecular weight isocyanates. Examples of low-molecular isocyanates suitable for treatment in accordance with present invention include:

a) monoisocyanates having aliphatically, cycloaliphatically, araliphatically or aromatically bonded isocyanate groups such as, for example, butyl isocyanate, stearyl isocyanate, cyclohexyl isocyanate, benzyl isocyanate, 2-phenylethyl isocyanate, phenyl isocyanate and any mixtures of these monoisocyanates;

b) diisocyanates within the molecular weight range of from about 140 g/mol to about 400 g/mol and having aliphatically, cycloaliphatically, araliphatically or aromatically bonded isocyanate groups such as, for example, 1,4-diisocyanatobutane, 1,6-diisocyanatohexane (HDI), 2-methyl-1,5-diisocyanatopentane, 1,5-diisocyanato-2,2-dimethylpentane, 2,2,4- or 2,4,4-trimethyl-1,6-diisocyanatohexane, 1,10-diisocyanatodecane, 1,3- and 1,4-diisocyanatocyclohexane, 1,3- and 1,4-bis (isocyanatomethyl)cyclohexane, 1-isocyanato-3,3,5-trimethyl-5-isocyanatomethylcyclohexane (isophorone diisocyanate, IPDI), 4,4'-diisocyanatodicyclohexylmethane, 1-isocyanato-1-methyl 4(3)-isocyanatomethylcyclohexane (IMCI), bis (isocyanatomethyl)-norbornane, 2-methylpentane 2,4-diisocyanate, 1,3- and 1,4-bis(2-isocyanatoprop-2-yl) benzene (TMXDI), 2,4- and 2,6-toluene diisocyanate (TDI), 2,4'- and 4,4'-diisocyanatodiphenylmethane, 1,5-diisocyanatonaphthalene, dipropylene glycol diisocyanate, 2,4- or 2,6-diisocyanato-1-methylcyclohexane and any mixtures of these diisocyanates, c) triisocyanates and/or higher functional isocyanates such as, for example, 4-isocyanatomethyl-1,8-octane diisocyanate (nonane triisocyanate), 1,6,11-undecane triisocyanate, 3-isocyanatomethyl-1,6-hexamethylene diisocyanate and any mixtures of these isocyanates.

Starting materials for the process according to the invention may, of course, also be mixtures of mono and/or di- and/or triisocyanates and/or of higher functional isocyanates.

In general, the low-molecular weight isocyanates used in the practice of the present invention may be any organic isocyanate having a molecular weight within the range of up to approximately 400 g/mol, preferably from 99 to 279 g/mol.

Preferably the above-mentioned difunctional and higher functional isocyanates are used in the process according to the invention. The use of 4-isocyanatomethyl-1,8-octane diisocyanate (nonane triisocyanate) is particularly preferred.

The gel-type or macroporous, anion-exchanging organic material useful in the process of the present invention may be any anion-exchanging organic material which contains tertiary and/or quaternary amino groups and is characterized in that it a) is largely free from water and from other solvents and admixtures which react with isocyanates, b) is free from functional groups which react with isocyanates, for example, alcohol groups, thiol groups, 1°- and 2°-amino groups and carboxylic groups, c) can be separated from the isocyanate(s) by conventional methods of separation such as filtration and/or extraction and/or distillation and d) is largely free from metal ions.

The gel-type or macroporous, anion-exchanging organic material may, for example, be a material containing tertiary and/or quaternary amino groups of the type which are described, for example, in *Ullmann* Vol. A14; p 393 ff), in DE-A 2,418,976 or in DE-A 2,211,134, and whose matrices are obtained by condensation (for example, phenol-formaldehyde) or by polymerization (for example, copolymers of styrene and divinylbenzene or of (meth)acrylates and divinylbenzene). Prior to being used in the process of the present invention, all of the above-mentioned anion-exchanging materials must be largely freed from water for the purpose of the process of the present invention.

Largely freed from water for the purpose of the process of the present invention means that the water content, as determined by Karl Fischer titration, is<5%, preferably<3% and most preferably<1%. This can be achieved by exchanging the water for an inert solvent which does not react with isocyanates or by drying the anion-exchanging materials, preferably under vacuum.

Largely free from solvents and admixtures which react with isocyanates and from metal ions means, in the process of the present invention, a content of such compounds of less than 5%, preferably less than 3% and most preferably less than 1%.

The anion-exchanging materials used in the process of the present invention can be used either as solids without solvent or in the form of a deposit in an inert solvent which does not react with isocyanates.

Among the anion-exchanging materials suitable for use in the process of the present invention are materials freed from water and from other solvents which react with isocyanates such as, for example: Lewatit® MP 62, MP 64, AP 49, M 510, M 511, M 610, MP 500, MP 600, AP 246, S 6328 A, S 5428 A (all commercially available from Bayer AG) or anion-exchanging Amberlite® or Duolite® (both commercially available from Rohm and Haas). Preferred materials for the purpose of the process according to the invention are the anion-exchanging organic materials described above whose matrices have been obtained by polymerization (copolymers of styrene and divinylbenzene and of (meth) acrylates and divinylbenzene). Anion-exchanging organic materials whose matrices have been obtained by polymerization (copolymers of styrene and divinylbenzene) and which contain tertiary amino groups are particularly preferred in the process of the present invention.

For purposes of the process of the present invention, "material" means a defined compound and mixtures of compounds, as well as polymeric compositions or mixtures of polymers characterized by a statistical molecular weight distribution, which meets the requirements given above. Mixtures of different materials may, of course, also be used in the process of the present invention.

The solid or macroporous anion-exchanging organic materials having tertiary and/or quaternary amino groups can be technical products which may, of course, albeit less preferably, still contain small proportions of free amines or amine salts or other secondary products.

The anion-exchanging materials used in the process of the present invention may, of course, be regenerated by suitable processing steps and reused.

In the process of the present invention, the mixture of organic isocyanate and at least 0.1% by weight, preferably from about 0.5 to about 50% by weight and most preferably from about 1.0 to about 10% by weight, based on the weight of isocyanate to be treated, of the gel-type or macroporous, anion-exchanging organic material having tertiary and/or quaternary amino groups is heated for at least 10 minutes, preferably from about 1 hour to about 24 hours, most preferably from about 3 hours to about 15 hours, at a temperature of <200° C., preferably from about 25° C. to about 200° C., more preferably from about 140° C. to about 190° C. and most preferably from about 150° C. to about 180° C. Optionally, the heated mixture may subsequently be treated to remove the purified low-molecular isocyanate from the gel-type or macroporous, anion-exchanging organic material having tertiary and/or quaternary amino groups and from any reaction products generated during heating of the mixture by filtration and/or by distillation and/or extraction and/or by other suitable methods of separation.

The process may, of course, also be carried out in a suitable inert solvent which does not react with isocyanates.

The isocyanate may be separated, during or after the heating, from the gel-type or macroporous, anion-exchanging organic materials having tertiary and quaternary amino groups and from any unwanted reaction products generated during the process, by filtration and/or by extraction and/or distillation and/or by other suitable methods of separation, optionally under vacuum. Preferably the purified isocyanate is separated from the gel-type or macroporous anion-exchanging organic materials having tertiary and/or quaternary amino groups and from reaction products thereof by filtration.

To avoid secondary reactions with air or with traces of water, the reactor can be maintained under vacuum (for example, 1 to 100 mbar), or covered with inert gas, for example, nitrogen. In principle, the use of inert gas is not, however, necessary.

It is also possible to cause heating of the isocyanate compounds with the described anion-exchanging materials by using a type of column technique in which the anion-exchanging organic material is used as the stationary phase and the corresponding isocyanate compound is passed through that stationary phase under given conditions. In this case, the heating time is to be equated with the average residence time of the isocyanate compound in the anion-exchanging organic material.

Before, during or after lowering the chlorine content by the process of the present invention, other purification methods may also be used in order, for example, to remove coloring components and secondary products. These other purification methods may include treatments and/or brightening processes, for example, with reducing or oxidizing agents and treatment with adsorbents such as activated carbon and/or bleaching agents and/or silicas. Brightening processes of this type may also have a positive effect on the lowering of the chlorine content of the isocyanate compound. The isocyanate which is obtained after the chlorine content has been lowered and is freed from the gel-type or macroporous, anion-exchanging organic material having tertiary and/or quaternary amino groups can in addition optionally be subjected, preferably under vacuum (for example, 0.001 mbar to 100 mbar), to a further purification by distillation (for example, batch distillation or distillation by means of a film evaporator).

Isocyanates purified in accordance with the present invention do not contain any harmful additives in the form of metal compounds, acids, bases or other compounds which react with isocyanates, and they have a hydrolyzable chloride content of preferably <180 ppm. These purified isocyanates can be used, for example, for the preparation of oligomeric polyisocyanates or prepolymers and, in the case of the triisocyanates, as starting materials for intermediate products, polyurethane molded parts and coating agents. The low-molecular triisocyanates purified by the process of the present invention are preferably used as curing components in coatings.

In principle, coating materials which contain isocyanates purified by the process of the present invention are suitable for coating any substrate. Examples of suitable substrates include: wood, plastics, leather, paper, textiles, glass, ceramic, plaster, masonry, metals and concrete. The coating material may be applied by conventional methods of application, such as spraying, painting, flow coating, casting, dipping, and rolling. The coating materials can be used in the form of clear lacquers and in the form of pigmented lacquers. They may be applied diluted in organic solvents or dispersed in water or undiluted as one-component or multi-component coatings.

EXAMPLES

The following Examples illustrate the invention. The HC values given refer to the content of hydrolyzable chlorine. All percentages given refer to percentages by weight.

The quantity of compound A, B, C or the mixture of A and C given in Table 1 or Table 2 is added to 100 g of the organic isocyanate and the resultant mixture is stirred under vacuum (10 to 100 mbar, depending upon the isocyanate used) for the time indicated in the Table and at the temperature indicated in the Table. After the given reaction time, the products are subjected to a filtration (Examples 3, 4, 5, 8 and 9) or to a filtration with subsequent film distillation (180° C./0.2 mbar) (Examples 6, 7). Products according to the invention are obtained.

TABLE 1

|  | Ex. 1* | Ex. 2*[1] | Ex. 3 | Ex. 4 | Ex. 5 |
| --- | --- | --- | --- | --- | --- |
| Organic isocyanate | TIN[2] | TIN[2] | TIN[2] | TIN[2] | TIN[2] |
| Additive used | — | Dibutyl-ammonium acetate | A | A | B |
| Wt. % of additive | — | 0.12 | 2.5 | 4.5 | 4.5 |
| Temperature | 170° C. | 225° C. | 170° C. | 170° C. | 170° C. |
| Reaction time [h] | 12 | 3 | 12 | 12 | 12 |
| HC value before conditioning [ppm] | 2064 | 2064 | 2064 | 2064 | 2064 |
| HC value after conditioning [ppm] | 1445 | 723 | 170 | 116 | 100 |
| NCO before heating [%] | 49.7 | 49.7 | 49.7 | 49.7 | 49.7 |
| NCO after heating [%] | 47.8 | 35.8 | 47.6 | 47.6 | 47.2 |

*Comparative Example
[1]Corresponds to first Example of DD 288 593.
[2]Triisocyanatononane.

Compound A: Lewatit® MP 62 (Bayer AG) in which water was exchanged for low-boiling solvents and subsequently dried at 25° C. under high vacuum.
Compound B: Lewatit® MP 64 (Bayer AG), in which water was exchanged for low-boiling solvents and subsequently dried at 25° C. under high vacuum.
Compound C: Lewatit® M 610 (Bayer AG) in which Lewatit was loaded with base, sodium chloride was washed out and water was exchanged, for low-boiling solvents and subsequently dried at 25° C. under high vacuum.

TABLE 2

|  | Ex. 6 | Ex. 7 | Ex. 8 | Ex. 9 |
| --- | --- | --- | --- | --- |
| Organic isocyanates | TIN[2] | TIN[2] | IPDI[3] | HDI[4] |
| Additive used | C | A&C | B | B |
| Wt. % of additive | 2.5 | 2.5 + 1.5 | 2.5 | 2.5 |
| Temperature | 170° C. | 170° C. | 170° C. | 170° C. |
| Reaction time [h] | 12 | 12 | 12 | 12 |
| HC value before conditioning [ppm] | 2064 | 2064 | 152 | 12 |
| HC value after conditioning [ppm] | 160 | 175 | 8 | 26 |
| NCO before heating [%] | 49.7 | 49.7 | 38.0 | 49.9 |
| NCO after heating [%] | 46.4 | 46.8 | 35.6 | 47.5 |

[2]Triisocyanatononane.
[3]Isophorone diisocyanate.
[4]Hexamethylene diisocyanate.

The difference in the NCO contents before and after heating provides information about unwanted secondary reactions and consequently about the loss in yield.

In Comparison Example 2 which is not according to the invention, the conditions described in the patent DD 288 593 were used to lower the HC content of TIN. The significant decrease in NCO points to an unacceptably high contamination.

Example 5 (process according to the invention): Even at 170° C., the HC content was lowered to 100 ppm under mild conditions, with only a small decrease in NCO.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for decreasing chlorine content of an isocyanate comprising contacting an isocyanate in which chlorine is present with at least 0.1 wt. % (based on weight of isocyanate) of a gel-type or macroporous anion-exchanging organic material containing tertiary and/or quaternary amino groups which is substantially free of metal ions, water and solvent for at least 10 minutes at a temperature less than 200° C.

2. The process of claim 1 in which the isocyanate in which chlorine is present is an isocyanate having a molecular weight of up to 400 g/mol.

3. The process of claim 1 in which the isocyanate from which chlorine has been removed is separated from the anion-exchanging material and any solvent or by-product.

4. The process of claim 3 in which the isocyanate is separated from the anion-exchanging material, solvent and by-products by filtration, distillation and/or extraction.

5. The process of claim 1 in which from 1.0 to 10.0 wt. % anion-exchanging material is added to the chlorine-containing isocyanate.

6. The process of claim 5 in which the chlorine-containing isocyanate and anion-exchanging material are heated to a temperature of from 150 to 180° C. for a period of from 3 to 15 hours.

7. The process of claim 6 in which the isocyanate from which chlorine has been removed is separated from the anion-exchanging material and any solvent or by-product by filtration.

8. The process of claim 3 in which the isocyanate from which chlorine has been removed is separated from the anion-exchanging material and any solvent or by-product by filtration.

9. The process of claim 1 in which the isocyanate from which chlorine is removed is 4-isocyanatomethyl-1,8-octane diisocyanate.

10. The process of claim 3 in which the hydrolyzable chlorine content of the isocyanate separated from the anion-exchanging material is less than 180 ppm.

* * * * *